United States Patent [19]

Dave et al.

[11] Patent Number: 4,626,537

[45] Date of Patent: Dec. 2, 1986

[54] GUANIDINES, PHARMACEUTICAL COMPOSITIONS AND USE

[75] Inventors: Krishna G. Dave; Thomas George, both of Bombay, India

[73] Assignee: Ciba-Geigy Corporation, Ardsley, N.Y.

[21] Appl. No.: 834,506

[22] Filed: Feb. 28, 1986

Related U.S. Application Data

[63] Continuation of Ser. No. 660,769, Oct. 19, 1984, abandoned, which is a continuation of Ser. No. 509,556, Jun. 30, 1983, abandoned, which is a continuation of Ser. No. 319,534, Nov. 9, 1981, abandoned, which is a continuation of Ser. No. 151,035, May 19, 1980, abandoned.

[30] Foreign Application Priority Data

May 29, 1979 [CH] Switzerland .......................... 4993/79

[51] Int. Cl.$^4$ ................... A61K 31/535; C07D 413/12
[52] U.S. Cl. ..................................... 514/237; 514/252; 514/326; 514/422; 540/480; 540/481; 540/482
[58] Field of Search ............... 260/243.3, 244.4, 245.5; 514/237, 252, 326, 422

[56] References Cited

U.S. PATENT DOCUMENTS

| | | | |
|---|---|---|---|
| 3,840,524 | 10/1974 | Grisar et al. | 260/239 B |
| 4,126,611 | 11/1978 | Grisar et al. | 260/239 B |
| 4,211,867 | 7/1980 | Rasmussen | 260/239 B |

OTHER PUBLICATIONS

Stowers, *British Medical Journal*, (1976) pp. 509-511.

*Primary Examiner*—Robert W. Ramsuer
*Attorney, Agent, or Firm*—Michael W. Glynn; Irving M. Fishman

[57] ABSTRACT

The invention relates to novel guanidine derivatives, particularly to substituted guanidines of the formula

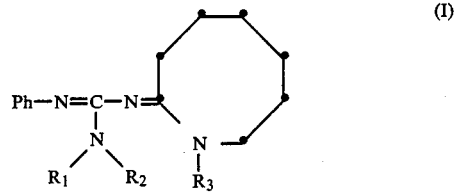

(I)

having hypoglycaemic activity, for the oral treatment of hyperglycaemia in mammals, especially for the oral treatment of Diabetes mellitus.

5 Claims, No Drawings

GUANIDINES, PHARMACEUTICAL COMPOSITIONS AND USE

This is a continuation of application Ser. No. 660,769, filed Oct. 15, 1984, now abandoned, which is a continuation of Ser. No. 509,556, filed June 30, 1983, now abandoned, which is a continuation of application Ser. No. 319,534, filed Nov. 9, 1981, now abandoned, which is a continuation of application Ser. No. 151,035, filed May 19, 1980, now abandoned.

The invention relates to novel guanidine derivatives of the formula I

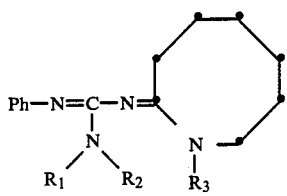
(I)

wherein Ph is a substituted or unsubstituted phenyl group, $R_1$ and $R_2$ independently of one another are each lower alkyl or cycloalkyl, or both taken together are a substituted or unsubstituted, bivalent hydrocarbon radical of aliphatic character, in which the carbon atoms of the chain can be interrupted by a hetero atom, and $R_3$ is hydrogen or lower alkyl; and to the tautomeric compounds and salts thereof.

In connection with the present specification, the radicals and compounds designated as "lower" contain preferably up to 7 carbon atoms, in particular up to 4 carbon atoms.

In the foregoing and in the following, the general definitions are as follows:

For example, $R_1$, $R_2$ and $R_3$ as lower alkyl groups are lower alkyl groups, and can be for example: methyl, ethyl, n-propyl, isopropyl n-butyl, isobutyl, sec-butyl, tert-butyl, n-pentyl, isopentyl, neopentyl, n-hexyl, isohexyl or n-heptyl groups.

A cycloalkyl group is in particular a monocyclic group having a 3–10 carbon atoms, preferably 5–7 carbon atoms, and is for example: a cyclopropyl, cyclobutyl, and preferably a cyclopentyl, cyclohexyl or cycloheptyl group.

The two substituents $R_1$ and $R_2$ taken together can be a bivalent aliphatic hydrocarbon radical which has 4–7 carbon atoms in the chain, and which is unsubstituted or is substituted by lower alkyl or by substituted or unsubstituted phenyl. The group —NR$_1$R$_2$ is for example lower alkyleneamino in which the lower alkylene chain can be interrupted for example by a hetero atom, such as oxygen or sulfur, or by nitrogen which is unsubstituted or is substituted by lower alkyl, or by substituted or unsubstituted phenyl, benzyl, phenylethyl or alkoxycarbonyl, for example methoxy or ethoxycarbonyl; and is for example: lower alkyleneamino, for example pyrrolidino, 2,5-dimethylpyrrolidino, piperidino, 2-methyl-, 4-methyl- or 4-phenylpiperidino, hexahydroazepino or octahydroazocino, oxa-lower-alkyleneamino, for example morpholino, 2,6-dimethylmorpholino, thia-lower alkyleneamino, for example thiomorpholino or 2,6-dimethylthiomorpholino and aza-lower-alkyleneamino, for example piperazino, N-methyl-, N-phenyl-N-benzyl, N-methoxycarbonyl- or N-ethoxycarbonylpiperazine.

Ph or an aforementioned, substituted or unsubstituted, phenyl group can be substituted by one, two or more identical or different substituents. Such substituents are for example hydrocarbon radicals, such as lower aliphatic hydrocarbon radicals, for example lower alkyl, optionally functionally modified hydroxyl or mercapto, such as etherified hydroxyl, for example lower alkoxy, lower alkenyloxy or lower alkylenedioxy, also lower alkylthio or halogen, trifluoromethyl, nitro, amino, including substituted amino, for example lower alkylamino or di-lower-alkylamino, substituted or unsubstituted sulfamyl, for example lower alkylsulfamyl or di-lower-alkylsulfamyl, optionally functionally modified carboxyl, such as esterified carboxyl, for example lower alkoxycarbonyl.

The lower alkyl groups applicable as substituents are defined in the foregoing for $R_1$, $R_2$ and $R_3$.

Lower alkoxy is for example: methoxy, ethoxy, n-propoxy, isopropoxy, n-butoxy or n-pentyloxy, and lower alkenyloxy, for example vinyloxy or allyloxy.

Halogen atoms are in particular fluorine, chlorine or bromine atoms; they can also be however iodine atoms.

Lower alkylthio is especially methylthio, also ethylthio, isopropylthio, n-propylthio, or straight-chain or branched-chain butylthio.

Lower alkylamino or di-lower-alkylamino is for example methylamino, dimethylamino, ethylamino, diethylamino, n-propylamino, di-n-propylamino, isopropylamino, di-isopropylamino or n-butylamino or di-n-butylamino.

Lower alkyl- or di-lower-alkylsulfamyl is for example methylsulfamyl, dimethylsulfamyl, ethylsulfamyl, diethylsulfamyl, n-propylsulfamyl, di-n-propylsulfamyl, isopropylsulfamyl, diisopropylsulfamyl, n-butylsulfamyl or di-n-butylsulfamyl.

By virtue of the existing tautomerism, the novel compounds according to the present invention can, in the case where $R_3$ is hydrogen, be in the tautomeric form. The tautomers can be expressed by the formulae

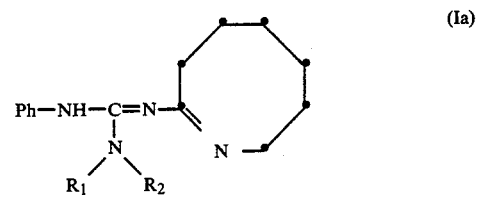
(Ia)

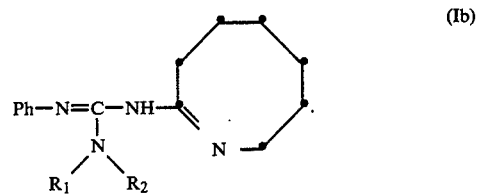
(Ib)

The novel compounds of the general formula I and their addition salts with inorganic or organic acids have valuable pharmacological properties, especially hypoglycaemic activity, as can be verified on rats having normal metabolism after oral administration of doses from 10 mg/kg, and also on rats which have been put into a diabetes-like metabolic condition by injection of streptozotocin [see A. Junod et al., Proc. Soc. Exp. Biol. Med. 126, 201–205 (1967)]. The lowering of the blood-sugar level is not accompanied by hyperlactataemia. Analogous effects can also be demonstrated on the guinea pig, hamster and rhesus monkey. The pharmacological findings characterise the novel compounds of the general formula I and pharmaceutically acceptable acid addition salts thereof as antidiabetics which can be used for the oral treatment of hyperglycaemia in mammals, particularly for the oral treatment of Diabetes mellitus.

The invention relates in particular to compounds of the formula I in which Ph is a substituted or unsubstituted phenyl group, $R_1$ and $R_2$ independently of one another are each a lower alkyl group, for example methyl, or ethyl or cycloalkyl, such as cyclopentyl, cyclohexyl or cycloheptyl, or $R_1$ and $R_2$ taken together are a bivalent hydrocarbon radical of aliphatic character which has 4–7 carbon atoms in the chain and which is unsubstituted or substituted by lower alkyl or phenyl, and in which the carbon atoms of the chain can be interrupted by a hetero atom, and $R_3$ is hydrogen or lower alkyl, and to the tautomeric compounds and salts thereof.

The invention relates in particular to those compounds of the formula I in which Ph is a phenyl group which is unsubstituted or substituted by lower alkyl, lower alkoxy, halogen or trifluoromethyl, $R_1$ and $R_2$ taken together are a lower alkylene chain which is unsubstituted or substituted by lower alkyl or by phenyl, in which chain the carbon atoms can be interrupted by a hetero atom, for example oxygen or sulfur, or nitrogen which is unsubstituted or substituted by lower alkyl, phenyl, benzyl, phenylethyl or alkoxycarbonyl, and $R_3$ is hydrogen or lower alkyl, and to the tautomeric compounds and salts thereof.

Of particular interest are compounds of the formula I in which Ph is a phenyl group which is unsubstituted or substituted by lower alkyl, lower alkoxy, halogen or trifluoromethyl, the group —$NR_1R_2$ is for example lower alkyleneamino which is substituted by lower alkyl or by phenyl, in which the lower alkylene chain can be interrupted by oxygen, sulfur, or nitrogen which is unsubstistuted or is substituted by lower alkyl, phenyl, benzyl or alkoxycarbonyl, and can be for example: pyrrolidino, 2,5-dimethylpyrrolidino, piperidino, 2-methyl-, 4-methyl- or 4-phenylpiperidino, hexahydroazepino, morpholino, 2,6-dimethylmorpholino, thiomorpholino, 2,6dimethylthiomorpholino, piperazino, N-methyl-, N-phenyl-, N-benzyl-, N-methoxy-, N-ethoxycarbonylpiperazine, and $R_3$ is hydrogen or lower alkyl, and the tautomeric compounds and salts thereof.

Of very particular interest are compounds of the formula I in which Ph is phenyl which is unsubstituted or is substituted by lower alkyl, such as methyl or ethyl, lower alkoxy, such as methoxy or ethoxy, halogen, such as chlorine or bromine, or trifluoromethyl, the group —$NR_1R_2$ is for example lower alkyleneamino which is substituted by lower alkyl, for example methyl or ethyl, or phenyl, in which the lower alkylene chain can be interrupted by oxygen, or by nitrogen which is unsubstituted or is substituted by lower alkyl, such as methyl or ethyl, or alkoxycarbonyl, such as methoxy- or ethoxycarbonyl, and can for example: pyrrolidino, piperidino, 4-methyl- or 4-phenylpiperidino, morpholino, 2,6-dimethylmorpholino, piperazino, N-methyl- or N-methoxycarbonylpiperazine, and $R_3$ is hydrogen or lower alkyl, for example methyl or ethyl, and the tautomeric compounds and salts thereof.

The novel guanidines of the formula I are obtained by methods known per se.

Thus, for example, the novel compounds of the formula I can be obtained by a process in which a compound of the formula II

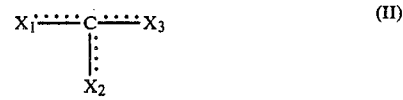 (II)

wherein $X_1$ is the group Ph—N=, in which Ph is a substituted or unsubstituted phenyl group as defined under formula I, or a group which can be split off, $X_2$ is the group —$NR_1R_2$, wherein $R_1$ and $R_2$ have the meanings defined under the formula I, or a group which can be split off, and $X_3$ is the group

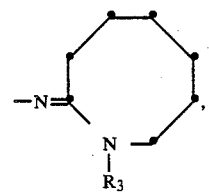

wherein $R_3$ has the meaning given under the formula I, or a group which can be split off, with the proviso that only one of the substitutents $X_1$, $X_2$ or $X_3$ can be a group which can be split off and wherein one of the groups $X_1$, $X_2$ or $X_3$ is attached by a double bond to the carbon atom, is reacted with an amine or imine, which corresponds to the missing amino or imino group defined under $X_1$, $X_2$ or $X_3$, in order to replace the group which can be split off; and, if required, additional process steps are performed; and/or, if required, compounds obtained are converted into salts; and/or, if required, resulting salts of compounds of the formula I are converted into the free bases.

Removable groups $X_1$, $X_2$ or $X_3$ are, as stated above, the groups which are replaceable by an amino or imino group, and are preferably lower alkylthio groups, for example methylthio or ethylthio, lower alkoxy, for example methoxy or ethoxy, or halogen, such as chlorine or bromine.

Compounds of the general formula II are, depending on whether the group which can be split off is $X_1$, $X_2$ or $X_3$, compounds of the formula IIa

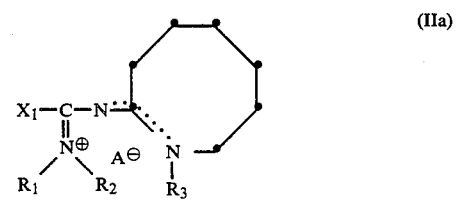 (IIa)

wherein $X_1$ is a group which can be split off, and $R_1$, $R_2$ and $R_3$ have the meanings given above and $A^\ominus$ is an anion, for example halide; or they are compounds of the formula IIb

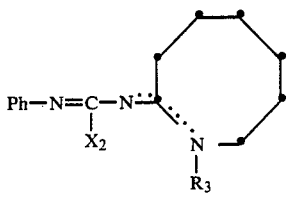

(IIb)

wherein $X_2$ is a group which can be split off, and Ph and $R_3$ have the meanings given above; or they are compounds of the formula IIc

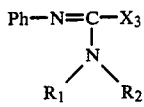

(IIc)

wherein $X_3$ is a group which can be split off, and Ph, $R_1$ and $R_2$ have the above given meanings; the tautomeric forms thereof, or the acid addition salts thereof.

Depending on whether $X_1$, $X_2$ or $X_3$ is present as the group which can be split off in a compound of the formula II, a compound of the formula IIb is reacted with an amine of the formula $HNR_1R_2$, a compound of the formula IIc with an imino compound of the formula III

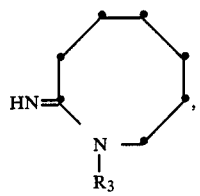

(III)

or a compound of the formula IIa with a substituted or unsubstituted aniline of the formula $Ph-NH_2$. Compounds of the formulae IIa, IIb and IIc can also be used as acid addition salts, preferably as hydrohalides. In an analogous manner, also the employed amines, imino compounds or anilines can be reacted as acid addition salts, preferably as hydrohalides.

The reaction of a compound of the formula II, that is to say, particularly of a compound of the formula IIa, IIb or IIc, for example with an aforementioned amine or imine as a free base is performed using a stoichiometric excess of the amine or imine, for example in a molar ratio of 1:1.05 to 1:2.0. With the use of only a slight excess of the amine or imine as free base, or with use of the amine or imine as acid addition salts, it is advantageous to add an additional stoichiometrically equivalent amount of the tertiary alkylamine, for example triethylamine or N-ethyldiisopropylamine.

When for example an imino compound of the formula III as free base

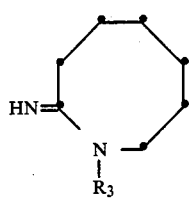

(III)

is reacted with a compound of the formula IIc in which $X_3$ is halogen, there are preferably used 2 molar equivalents or more of the free base of the above-mentioned imino compound. According to the following reaction pattern

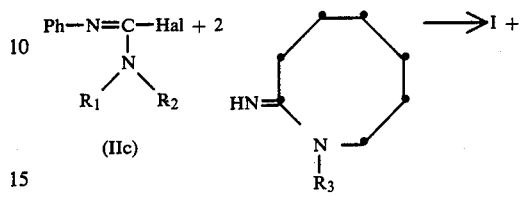

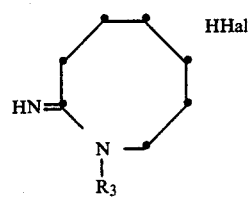

there is formed one equivalent of the imino compound as acid addition salt. For this reason, the reaction is preferably performed in an aprotic solvent in which the resulting compound of the formula I is soluble, whereas the addition salt of the hydrohalic acid according to the above reaction pattern precipitates as an insoluble compound. In this manner, the two reaction products obtained can be easily separated by simple filtration. The resulting acid addition salt of the imino compound is converted by basic hydrolysis, for example by the addition of an hydroxide or carbonate of alkali metals or alkaline-earth metals, into the free base, and can thus be re-used as starting product. Preferably, however, compounds of the formulae IIc and III are reacted as acid addition salts, for example as halides, as mentioned above in the presence of an additional tertiary alkylamine, for example triethylamine or N-ethyldiisopropylamine.

The described reactions of compounds of the formula IIc with an imino compound of the formula III are performed, as already mentioned, preferably in aprotic solvents. Examples of solvents preferably used are ethers, such as diethyl ether and tetrahydrofuran, lower aliphatic ketones and esters, such as acetone, methyl ethyl ketone and ethyl acetate, aromatic hydrocarbons, for example benzene, toluene or xylene, as well as acetonitrile. The reaction is however particularly preferably carried out in diethyl ether or in acetonitrile. The reactions can be performed at a temperature of between 0° to 150° C., preferably however between room temperature and the reflux temperature of the reaction mixture.

When however the employed starting compound of the formula II is for example a compound of the formula IIb

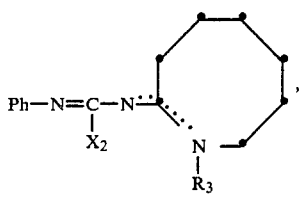

(IIb)

$X_2$ as a group which can be split off is preferably a lower alkoxy or lower alkylthio group. Starting compounds of the formula IIb are reacted in the form of their salts, for example in the form of their acid addition salts with a hydrohalic acid, with an amine of the formula $HNR_1R_2$ as free base or as acid addition salt, in which $R_1$ and $R_2$ have the meanings already defined.

The reactions are performed for example in an alcohol as solvent, preferably in a lower alkanol, such as ethanol, isopropanol or tert-butanol, particularly preferred however in an ether, for example diethyl ether or tetrahydrofuran, or in acetonitrile, at a temperature of between room temperature and preferably reflux temperature of the reaction mixture. The reactions can be performed however in a closed reaction vessel under pressure, for example in a bomb tube or in an autoclave, at elevated temperatures. The guanidine derivates of the formula I are obtained in the form of their salts, which can be converted for example by alkaline hydrolysis into the corresponding free bases. In the reaction of the compounds of the general formula IIb with the amine of the general formula $HNR_1R_2$, the amine is preferably used in a stoichiometric excess, for example in a molar ratio of 1:1.05 to 1:2.0 and higher. With use of only a slight excess of the amine or of an acid addition salt, it can be of advantages to add an additional stoichiometrically equivalent amount of a tertiary alkylamine, such as triethylamine or N-ethyldiisopropylamine, in order to increase the rate of reaction.

The reactions of compounds of the formula IIa with a group $X_1$ which can be split off, which besides being a halogen atom is preferably lower alkoxy or lower alkylthio, or of the tautomeric form thereof, with a substituted or unsubstituted aniline as free base, are performed in the same manner as described in the case of the reaction of a compound of the formula IIb with an amine of the formula $HNR_1R_2$. The reactions are advantageously performed also in a stoichiometric excess of the substituted or unsubstituted aniline. With use of only a slight excess of aniline or of an acid addition salt thereof, it can be advantageous to add a stoichiometrically equivalent amount of a tertiary trialkylamine already defined in the foregoing. The reactions are performed in solvents analogous to those previously described in the case of the reaction of compounds IIc with compounds of the formula III.

Compounds of the general formula II can be produced also by reacting a guanidine compound of the general formula IV

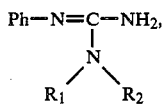

(IV)

wherein Ph, $R_1$ and $R_2$ have the meanings defined under the formula I, with a compound of the general formula V

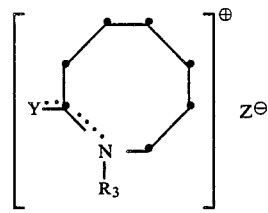

(V)

wherein Y is lower alkoxy, such as methoxy or ethoxy, lower alkylthio, such as methylthio or ethylthio, halogen, such as chlorine or bromine, or Y denotes two lower alkoxy groups which are located on the same C atom, and Z is a tetrafluoroborate anion, a fluorosulfonate anion, a lower alkylsulfate anion, such as a methylsulfate or alkanesulfonate anion, for example a methanesulfonate anion, or a halide, for example chloride or bromide, where, if Y denotes two lower alkoxy groups on the same C atom, Z as an anion is not present, or, if $R_3$ is hydrogen, the tautomeric form occurs as free base; and, if required, additional process steps are performed, and/or, if required, converting a resulting compound of the formula I into a salt; and/or, if required, converting a resulting salt of a compound of the formula I into the free compound.

The compounds of the general formula I are advantageously produced by reacting, in stoichiometric amounts, a lactam salt of the formula V given in the foregoing with a guanidine derivative of the above formula IV. The reactions are preferably performed in an anhydrous organic solvent. Organic solvents are for example: lower alkanols, such as methanol, ethanol, isopropanol, tert-butanol, ethers, such as diethyl ether, tetrahydrofuran or dioxane, lower halogenated hydrocarbons, such as chloroform, methylene chloride or 1,2-dichloroethane, and aromatic hydrocarbons, such as benzene, toluene or xylene. The reaction is in general performed at temperatures between $-20°$ C. and $+50°$ C., preferably however between $0°$ C. and room temperature.

The reaction product of the general formula I obtained in salt form is converted into the free base by basic hydrolysis, for example by addition of a hydroxide or carbonate of an alkali metal or alkaline-earth metal.

The lactam fluoroborates or lactam fluorosulfonates of the general formula V, which are used according to the process, in which $Z^\ominus$ is the tetrafluoroborate group of the formula $BF_4^\ominus$ or the fluorosulfonate group of the formula $OSO_2F^\ominus$, can be produced by customary processes comprising reacting a lactam of the formula Va

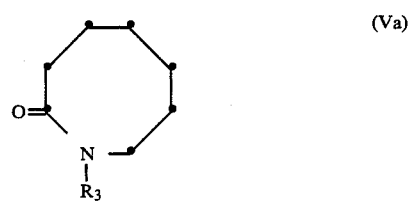

(Va)

with an appropriate trialkyloxonium fluoroborate or with a fluorosulfonic acid lower alkyl ester to give the corresponding lactam salt of the general formula V.

The reaction is performed for example at temperatures between −20° C. and +50° C., preferably at temperatures between 0° C. and +25° C., in an inert gas, for example in nitrogen or argon, and in the presence of an inert anhydrous organic solvent, for example in a lower halogenated hydrocarbon, such as chloroform, 1,2-dichloroethane or preferably methylene chloride. Examples of other applicable organic solvents are ethers, such as diethyl ether, dioxane, tetrahydrofuran or 1,2-dimethoxyethane, as well as aromatic hydrocarbons, for example benzene, toluene or xylene.

The 2-lower-alkylthiolactim ethers embraced by the general formula V can be produced by reaction of the lactam of the general formula Va with phosphorus pentasulfide by a process analogous to that described by R. Gomper et al., Org. Syn. Coll., Vol. V, pp. 780–785. On carrying out this reaction, there is firstly obtained a thiolactam which, by reaction with an alkylating agent, yields the 2-alkylthiolactim ether in the form of the corresponding salts. The alkylating agent used can be an alkyl halide, for example methyl iodide, a fluorosulfonic acid alkyl ester, such as fluorosulfonic acid methyl ester, a methanesulfonic acid alkyl ester, such as methanesulfonic acid methyl ester, a toluenesulfonic acid alkyl ester, such as toluenesulfonic acid methyl ester, or dimethyl sulfate. The reaction of the lactim ether salts with the guanidine derivative of the general formula IV yields the corresponding salts of the general formula I.

In the reaction of the previously described lactam fluorosulfonates of the general formula V with the guanidines of the general formula IV, there can be formed, as a secondary reaction, also quaternary ammonium salts of the compounds of the general formula I.

The methylsulfate salts also embraced by the general formula V are obtained, in a manner analogous to that described by H. Bredereck et al., Chem. Ber. Vol. 96 (1963), p. 1350, for pyrrolidones, from lactams of the general formula Va by reaction with dimethyl sulfate. The reaction is preferably performed in an anhydrous, inert organic solvent, for example in an aromatic hydrocarbon, such as benzene, toluene or xylene, in an ether, such as diethyl ether, dioxane or tetrahydrofuran, or in a halogenated aliphatic hydrocarbon, such as 1,2-dichloroethane or chloroform. The resulting methylsulfate of the general formula V is then converted with the appropriate guanidine derivative of the general formula IV, in the manner described in the foregoing, into the corresponding lower alkyl sulfate salt, for example methylsulfate salt of the compound of the general formula I. The salts obtained can be converted, by treatment with a hydroxide or carbonate of an alkali metal or alkaline-earth metal, into the corresponding free bases of the general formula I.

From the lower alkyl sulfate salt, such as the methylsulfate salt, of the general formula V, there can be produced, for example by reaction with a metal alkoxide, preferably with an alkali metal alkoxide, such as sodium methoxide or ethoxide, in an appropriate anhydrous lower alkanol, the corresponding lactam acetal of the formula Vb

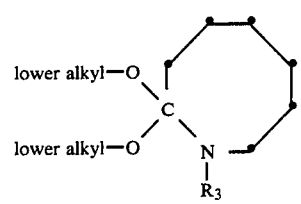

The free bases of the general formula I can be obtained, in the manner described in the foregoing, from the lactam acetals by reaction with the guanidine derivatives of the general formula IV.

The halide salts, particularly chloride salts, of the lactams of the general formula V, used according to the process, can be produced, in a manner analogous to that described by W. Jentsch and M. Seefelder, Chem. Ber., Vol. 98 (1965), p. 274, for pyrrolidones, by reaction of a lactam of the general formula Va with phosgene or with thionyl chloride.

As already mentioned in the foregoing, there can be used for producing compounds of the general formula I in which $R_3$ is a hydrogen atom also the free bases of the general formula V. The reaction of the salts of the general formula V with a base, for example with a hydroxide or carbonate of an alkali metal or alkaline-earth metal, preferably in a halogenated aliphatic hydrocarbon as the solvent, such as methylene chloride or chloroform, yields the free bases of the general formula Vc

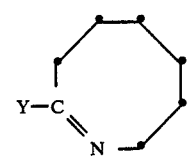

The compounds of the formula I according to the invention, in which $R_1$ has the meaning defined above, and $R_2$ and/or $R_3$ are (is) hydrogen, can be converted, using a third process, by reaction with an alkylating agent, into compounds of the formula I in which $R_2$ and/or $R_3$, within the scope of the definition for $R_2$ and $R_3$ given in the foregoing, have a meaning other than hydrogen; and, if required, additional process steps can be performed; and/or, if required, resulting compounds of the formula I are converted into a salt; and/or, if required, resulting salts of compounds of the formula I are converted into free bases.

The alkylating agent used can be for example: an alkyl halide, such as methyl iodide, a fluorosulfonic acid alkyl ester, such as fluorosulfonic acid methyl ester, a methanesulfonic acid alkyl ester, such as methanesulfonic acid methyl ester, a toluenesulfonic acid alkyl ester, such as toluenesulfonic acid methyl ester, or dialkyl sulfate, such as dimethyl sulfate.

The compounds of the formula I according to the invention in which $R_2$ and/or $R_3$ are (is) hydrogen can be produced, using a fourth process in which, in compounds of the general formula VI

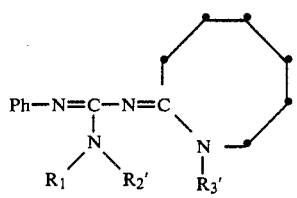

(VI)

wherein $R_1$ and Ph have the meanings given under the formula I, and one of the substituents $R_2'$ and $R_3'$ has the meaning of $R_2$ or $R_3$, and the other is an amino protecting group, or both $R_2'$ and $R_3'$ are each an amino protecting group, the amino protecting group is split off; and, if required, additional process steps are performed; and, if required, resulting compounds of the formula I are converted into salts; and/or, if required, resulting salts of compounds of the formula I are converted into the free bases.

An amino protecting group $R_2'$ and $R_3'$ is in particular an acyl group, such as acyl of an aliphatic, aromatic or araliphtic carboxylic acid, especially lower alkanoyl, for example acetyl or propionyl, or aroyl, for example benzoyl or acyl of formic acid or of a carbonic acid half-derivative, for example a carbonic acid half-ester, such as formyl, lower alkoxycarbonyl, for example ethoxycarbonyl or tert-butyloxycarbonyl, or aryl-lower-alkoxycarbonyl, for example benzyloxycarbonyl.

The splitting-off of an acyl group used as an amino protecting group $R_2'$ and/or $R_3'$ is effected in a manner known per se, for example by solyvolysis, in particular by means of alcoholysis, also by means of hydrolysis. The alcoholytic splitting-off of an acyl group $R_2'$ and/or $R_3'$ can be performed for example in the presence of a strongly basic agent, at elevated temperature, for example at about 50° C. to about 120° C. There is used in particular a lower alkanol, for example n-butanol or ethanol, and as a strong base an alkali metal lower alkanolate, for example sodium or potassium lower alkanolate, for example -n-butylate or -ethylate, or an alkali metal hydroxide, for example sodium or potassium hydroxide.

Amino protecting groups $R_2'$ and $R_3'$, for example lower alkoxycarbonyl groups, such as tert-butyloxycarbonyl, can be particularly gently acidolytically split off, for example by treatment with trifluoroacetic acid.

A further amino protecting group which can be split off in a particularly gentle manner is an ethoxycarbonyl group which carries in the β-position a silyl group substituted with three hydrocarbon radicals, such as a triphenylsilyl, dimethyl-butyl-silyl or, in particular, trimethylsilyl group. A β-(tri-methylsilyl)-ethoxycarbonyl group of this type forms with the amino group to be protected a corresponding β-tri-methylsilylethoxycarbonylamino group, which can be split off under mild conditions by the action of fluoride ions. Suitable reagents releasing fluoride ions are for example fluorides of quaternary organic bases, such as tetraethylammonium fluoride.

It is to be ensured that as amino protecting groups $R_2'$ and/or $R_3'$ there are used only those groups which can be split off selectively whilst retaining the structure of the compounds of the general formula I.

The starting materials are known, or in the case where they are novel they can be produced by methods known per se. Where it is shown to be useful, the employed starting products have already been described subsequent to the described process.

Compounds of the general formula IIb in which $X_2$ is a lower alkylthio group can be produced for example from the corresponding thioureas of the general formula VII

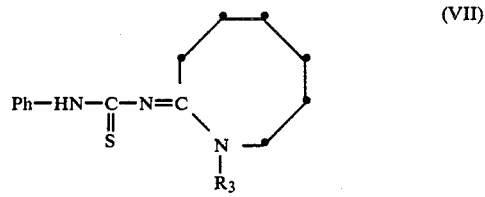

(VII)

by reacting these with an aforementioned alkylating agent of the formula $R_xZ_y$ in which $R_x$ is a lower alkyl group, for example a methyl or ethyl group, and $Z_y$ is for example a-ptoluenesulfonate, lower alkanesulfonate as for example methanesulfonate, fluorosulfonate, or lower alkylsulfate, as for example methylsulfate group or preferably a halide.

The reaction is performed in an organic solvent already defined in the foregoing. The solvent preferably used in an ether, such as diethyl ether, tetrahydrofuran or dioxane, a ketone, for example acetone or 2-butanone, a halogenated aliphatic hydrocarbon, such as chloroform or methylene chloride, or a lower alkanol, such as methanol or ethanol. An alkyl halide in methanol or ethanol is particularly suitable. The alkylating agent is generally used in at least an equimolar amount alkylation can optionally be performed at room temperature or at elevated temperatures, and if necessary in a closed reaction vessel.

Compounds of the general formula VII on the other hand can be produced from the already mentioned and known imino compounds of the formula III

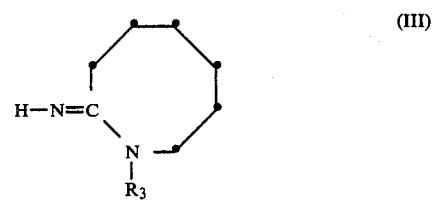

(III)

by reaction with a substituted or unsubstituted phenylisothiocyanate of the formula Ph—NCS in an inert organic solvent, preferably in benzene, methylene chloride or chloroform, at temperatures of 0° C. to room temperature for 2–24 hours in approximately equimolar amounts.

Compounds of the formula IIc in which $X_3$ as a removable group is halogen, preferably chlorine, are obtained, using the method described by E. Kühle, Angew. Chem., Intern. Ed., Vol. 8 (1969), pp. 24–26, by reacting an isocyanide dihalide of the formula VIII

(VIII)

with an amine of the formula $HNR_1R_2$ ind the presence of an additional trialkylamine, for example triethylamine, in an inert aprotic, anhydrous solvent. Compounds of the formula VIII can also occur as immonium chlorides. The solvent used is for example an ether, for example diethyl ether, dioxane or tetrahydrofuran, a halogenated aliphatic hydrocarbon, such as chloroform or methylene chloride, or an aromatic hydrocarbon, for example benzene, tolune or xylene. Compounds of the general formula VIII are known, and can be produced in a manner analogous to that described in Angew. Chem., Intern. Ed. Vol. 6 (1967), p. 649.

Compounds of the general formula IIc in which the removable group $X_3$ is halogen can be readily converted, in a known manner, into compounds of the formula IIc in which $X_3$ is a lower alkoxy group.

Starting compounds of the general formula IIa in which the removable group $X_1$ is halogen, preferably chlorine, can be produced by reaction of an immonium chloride of the formula

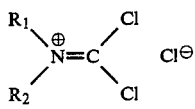

with an imino compound of the formula III

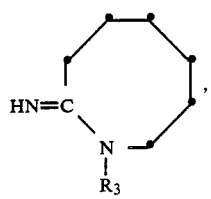

using the process described by R. G. Glushkow, Khim.-Farmasevt. Zh. 12, No. 6, 59–64/1978.

The reaction is performed in a manner analogous to that described above in the case of the reaction of a compound of the formula VIII.

Compounds of the general formula VI can be produced by one of the processes described in the foregoing for the production of compounds of the general formula I, $R_2$ and/or $R_3$ in the employed starting products being however an acyl group. These acyl groups used as amino protective groups are as defined above.

The described processes can be performed, in the customary manner, at room temperature, with cooling or heating, under normal pressure or elevated pressure and, if required, in the presence or absence of a diluent, catalyst or condensation agent. When necessary, the reactions can also be carried out in the atmosphere of an inert gas, for example nitrogen.

In the compounds obtained, it is possible within the scope of the definitions of the final products to introduce, modify or split off substituents. Starting compounds and processes for their production are also part of the invention if they are new.

Depending on the process conditions and starting materials, the final products are obtained in the free form or in the form of their salts, particularly acid addition salts, which are likewise embraced by the invention. The acid addition salts of the novel compounds can be converted, in a manner known per se, into the free compounds, for example with basic agents, such as alkalies or ion exchangers. Conversely, the free bases obtained can form salts with organic or inorganic acids. For producing acid addition salts, the acids used are in particular acids which are suitable for forming therapeutically applicable salts. The following may be mentioned as examples of suitable acids: hydrohalic acids, sulfuric acids, phosphoric acids, nitric acid, perchloric acid, aliphatic alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulfonic acid, ethanesulfonic acid, hydroxyethanesulfonic acid or ethylenesulfonic acid; halogenobenzenesulfonic acid, toluenesulfonic acid, naphthalenesulfonic acid or sulfanilic acid; and methionine, trypthophane, lysine or arginine.

These or other salts of the novel compounds, for example the picrates, can also be used to purify the free bases obtained, the process comprising converting the free bases into salts, separating these, and liberating the bases again from the salts. Because of the close relationship between the novel compounds in the free from and in the form of their salts, what is stated in this specification in respect of the free compounds also applies by analogy to the corresponding salts.

The invention also relates to those embodiments of a process in which a process is discontinued at any stage, or in which a compound obtainable as an intermediate at any stage is used as the starting material and the uncompleted stages are carried out, or in which a starting material is formed under the reaction conditions or, if required, is used in the form of a salt. The invention also includes intermediates resulting therefrom.

Also embraced by the invention are therapeutic compositions consisting of a hypoglycaemically effective proportion of the compounds of the general formula I or of an acid addition salt thereof, and a pharmacologically acceptable solid carrier or liquid diluent.

The pharmaceutical preparation according to the invention contain at least one compound of the general formula I, or a salt thereof, as active substance, together with a customary pharmaceutical carrier. The type of carriers is governed largely by the field of application. The pharmaceutical compositions according to the invention which contain as active substances compounds of the formula I can be administered orally, parenterally or rectally.

Suitable for oral treatment of hyperglycaemia are in particular solid dosage units, such as tablets, dragées and capsules, which preferably contain between 10 and 90% of an active substance of the general formula I or of a salt thereof in order to render possible the administration of daily doses of between 1.5 and 100 mg/kg to warm-blooded animals. Tablets and dragée cores are produced by combining the compounds of the general formula I with solid pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of suitable molecular weight. Dragée cores are subsequently coated for example with concentrated sugar solutions which can also contain for example gum arabic, talcum and/or titanium dioxide, or with a lacquer dissolved in readily volatile organic solvents or solvent mixtures. Colouring agents may be added to these coatings, for example for indentification of the various dosage amounts. Soft gelatine capsules and other closed capsules consist for example of a mixture of gelatine and glycerin, and can contain for example mixtures of a compound of the formula I with polyethylene glycol. Hard gelatine capsules contain for example granulates of an active substance with solid pulverulent carriers, such as lactose, saccharose, sorbitol or mannitol; starches, such as potato starch, maize starch or amylopectin, cellulose derivatives, as well as magnesium stearate or stearic acid.

Suitable dosage units for rectal adminstration are for example suppositories which consist of a combination of an active substance with a suppository foundation substance based on natural or synthetic triglycerides (for example cocoa butter), polyethylene glycols or suitable higher fatty alcohols; and gelatine rectal capsules which contain a combination of the active substance with polyethylene glycols.

Ampule solutions for parenteral administration, especially intramuscular or intravenous administration, contain a compound of the formula I, or a salt thereof, at a concentration preferably of 0.5 to 5%, in the form of an aqueous dispersion prepared with the aid of customary solubility-promoting agents and/or emulsifiers, and optionally stabilisers; or preferably an aqueous solution of a pharmaceutically acceptable, water-soluble acid addition salt of a compound of the general formula I.

For liquids to be taken orally, such as syrups and elixiers, the concentration of active substance is chosen to ensure that a single dose can be easily measured out, for example as the content of a tea-spoon or of a mesauring spoon, for example 5 ml, or as a multiple of these amounts.

The following Examples (a) to (e) are intended to illustrate some typical forms of application, but in no way do they represent the only embodiments thereof.

(a) 250.0 g of active substance is mixed with 550.0 g of lactose and 292.0 g of potato starch; the mixture is then moistened with an alcoholic solution of 8 g of gelatine, and is granulated through a sieve. The granulate is dried, and 60.0 g of talcum, 10.0 g of magnesium stearate and 20.0 g of colloidal silicon dioxide are mixed in, and the mixture is pressed to form 10,000 tablets each weighing 125 mg and each containing 25 mg of active substance, and the tablets can be provided with grooves for a more precise adjustment of the dosage amount.

(b) A granulate is prepared from 100.0 g of active substance, 379 g of lactose and the alcoholic solution of 6.0 of gelatine; after drying, the granulate is mixed with 10.0 g of colloidal silicon dioxide, 40.0 g of talcum, 60.0 g of potato starch and 5.0 g of magnesium stearate, and the mixture is pressed out to form 10,000 dragée cores. These are subsequently coated with a concentrated syrup prepared from 533.5 g of crystallised saccharose, 20.0 g of shellac, 75.0 g of gum arabic, 250.0 g of talcum, 20.0 g of collodial silican dioxide and 1.5 g of colouring agent, and finally dried. The dragées obtained each weigh 150 mg and each contain 10 mg of active substance.

(c) 25.0 g of active substance and 1975 g of finely ground suppository foundation substance (for example cocoa butter) are thoroughly mixed and then melted. The melt is maintained homogeneous by stirring whilst 1000 2.0 g suppositories each containing 25 mg of active substance are being poured.

(d) To prepare a syrup having a content of active substance of 0.25%, there are dissolved in 3 liters of distilled water 1.5 liters of glycerin, 42 g of p-hydroxybenzoic acid methyl ester, 18 g of p-hydroxybenzoic acid-n-propyl ester and, with slight warming, 25.0 g of active substance; to this solution are then added 4 liters of 70% sorbitol solution, 1000 g of crystallised saccharose, 350 g of glucose and an aroma substance, for example 250 g of "Orange Peel Soluble Fluid", Eli Lilly and Co., Indianapolis, or 5 g of natural lemon aroma and 5 g of "half and half" essence, both from Haarmann and Reimer, Holzminden, Germany; the solution obtained is filtered, and the filtrate is subsequently made up with distilled water to 10 liters.

(e) To prepare a drip solution containing 1.5% of active substance, 150.0 g of active substance and 30 g of sodium cyclamate are dissolved in a mixture of 4 liters of ethanol (96%) and 1 liter of propylene glycol. A mixture of 3.5 liters of 70% sorbitol solution and 1 liter of water is prepared separately and then added to the above solution of active substance. An aroma substance, for example 5 g of cough-sweet aroma or 30 g of grapefruit essence, both from Haarmann and Reimer, Holzminden, Germany, is added; the whole is well mixed, filtered, and made up with distilled water to 10 liters.

The Examples which follow further illustrate the production of the novel compounds of the general formula I, but in no way do they limit the scope of the invention. The temperature values are in degrees Centigrade.

EXAMPLE 1

4 g of 1-aza-2-methoxy-1-cyclooctene is added to a suspension of 8 g of N-phenyl-1-pyrrolidinecarboximideamide hydroiodide in 30 ml of acetonitrile. The mixture is heated for 12 hours, with vigorous stirring, on a water bath. The acetonitrile is evaporated off under reduced pressure, and the residue is recrystallised from a mixture of acetone/ethyl acetate to yield N-hexahydro-2(1H)-azocinylidene-N'-phenyl-1-pyrrolidinecarboximide-amide-hydroiodide of the formula

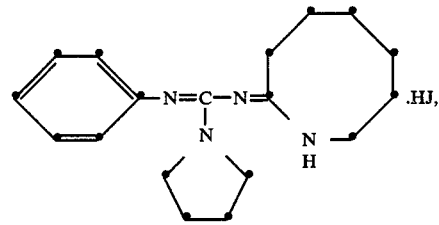

which melts at 242°.

The starting material for the above synthesis is produced as follows: 7 g of pyrrolidine is added to a suspension of 15 g of N-phenyl-S-methyl-isothiourea hydroiodide in 50 ml of acetonitrile. The mixture is refluxed with stirring for 15 hours. The acetonitrile is evaporated off under reduced pressure, and the residue is recrystallised from a mixture of isopropanol/ethyl ester to obtain N-phenyl-1-pyrrolidinecarboximide-amide-hydroiodide which melts at 165°.

EXAMPLE 2

3 g of 1-aza-2-methoxy-1-cyclooctene is added to a suspension of 6 g of N-phenyl-1-piperidinecarboximideamide hydroiodide in 20 ml of acetonitrile. The mixture is refluxed with vigorous stirring for 12 hours on a water bath. The acetonitrile is evaporated off under reduced pressure, and the residue is recrystalised from a mixture of isopropanol/ethyl acetate to yield N-hexahydro-2(1H)-azocinylidene-N'-phenyl-1- piperidinecarboximideamide-hydroiodide, which melts at 205°.

The starting material is produced as follows: 8 g of piperidine is added to a suspension of 15 g of N-phenyl-S-methyl-isothiourea-hydroiodide in 50 ml of acetonitrile. The mixture is refluxed with stirring for 15 hours. The acetonitrile is evaporated off under reduced pressure, and the mixture is recrystallised from a mixture is isopropanol/ethyl acetate to obtain N-phenyl-1-piperidinecarboximideamide-hydroiodide, which melts at 135°.

EXAMPLE 3

5.6 g of 3,4,5,6,7,8-hexahydro-2-methoxyazocine is added to a suspension of 10 g of N-phenyl-4-morpholinecarboximideamide-hydroiodide in 15 ml of acetonitrile. The mixture is heated with vigorous stirring on a water bath for 12 hours. The acetonitrile is evaporated off under reduced pressure, and the residue is recrystallised from a mixture of acetone/ethyl acetate to yield N-hexahydro-2(1H)-azocinylidene-N'-phenyl-4-morpholinecarboximideamide-hydroiodide, which melts at 260°.

The corresponding base and its salts are produced as follows: 10 ml of a 10% aqueous sodium hydroxide solution is added, with stirring, to a suspension of 4 g of N-hexahydro-2(1H)-azocinylidene-N'-phenyl-4-morpholine-carboximide-amide-hydroiodide in 50 ml of methylene chloride. The organic layer is separated, and concentrated by evaporation under reduced pressure to obtain the free base which melts at 130° after recrystallisation from a mixture of methylene chloride/hexane.

TARTRATE 2 g of previously dried and purified d-tartaric acid in acetone is added to a solution of 3.1 g of the free base in 30 ml of acetone. The product which has precipitated is repeatedly washed with diethyl ether and acetone. The residue is recrystallised from acetone to obtain N-hexahydro-2(1H)-azocinylidene-N'-phenyl-4-morpholinecarboximideamide tartrate, which melts at 105°.

SULFATE 10 g of sulfuric acid in methylene chloride is added with stirring to a solution of 3 g of the free base in 30 ml of methylene chloride/acetone. The product precipitates in the form of white crystals. Recrystallisation from a mixture of isopropanol/acetone yields N-hexahydro-2(1H)-azocinylidene-N'-phenyl-4-morpholinecarboximideamide sulfate, which melts at 210°.

p-TOLUENESULFONATE 1.8 g of p-toluenesulfonic acid is added with stirring to a solution of 3.2 g of the free base in 30 ml of methylene chloride/acetone. The product precipitates out in the form of colourless crystals. Recrystallisation from isopropanol yields N-hexahydro-2(1H)-azocinylidene-N'-phenyl-4-morpholine-carboximideamide-p-toluenesulfonate, which melts at 198°.

HYDROCHLORIDE

A solution of 4 g of the free base in 40 ml of isopropanol is acidified with hydrochloric acid in isopropanol. The solution is concentrated by evaporation under reduced pressure, and the residue is recrystallised from a mixture of isopropanol/acetone to yield N-hexahydro-2(1H)-azocinylidene-N'-phenyl-4-morpholine-carboximideamide hydrochloride, which melts at 210°.

METHANESULFONATE 0.5 g of methanesulfonic acid in methylene chloride is added to a solution of 1.6 g of the free base in methylene chloride. The product precipitates in the form of colourless crystals. Recrystallisation from a mixture of methanol/acetone yields N-hexahydro-2(1H)-azocinylidene-N'-phenyl-4-morpholine-carboximideamidemethanesulfonate, which melts at 212°.

The starting material used in this synthesis is produced as follows: 11 g of morpholine is added to a suspension of 29 g of N-phenyl-S-methyl-isothiourea hydroiodide in 90 ml of acetonitrile. The mixture is stirred and refluxed for 15 hours. The acetonitrile is evaporated off under reduced pressure, and the residue is recrystallised from a mixture of methylene chloride/ethyl acetate to obtain 1-(4-morpholinyl)-N-phenylcarboximideamide-hydroiodide, which melts at 182°.

EXAMPLE 4

2 g of 3,4,5,6,7,8-hexahydro-2-methoxyazocine is added with stirring to a suspension of 4 g of 4,N-diphenylpiperidine-carboximide-amide-hydroiodide in 15 ml of acetonitrile. The mixture is heated and vigorously stirred on a water bath for 12 hours. The acetonitrile is evaporated off under reduced pressure, and the residue is recrystallised from a mixture of acetone/ethyl acetate to yield N-hexahydro-2(1H)-azocinylidene-4,N'-diphenylpiperidine-carboximide-amide-hydroiodide, which melts at 228°–230°.

The starting materials for this synthesis is produced as follows: 7 g of 4-phenyl-piperidine is added with stirring to a suspension of 10 g of N-phenyl-S-methylisothiourea-hydroiodide in 30 ml of acetonitrile. The mixture is refluxed for 15 hours. The acetonitrile is evaporated off under reduced pressure, and the residue is recrystallised from a mixture of isopropanol/ethyl acetate to obtain 4,N-diphenylpiperidine-carboximideamide-hydroiodide, which melts at 151°.

EXAMPLE 5

1.5 g of 3,4,5,6,7,8-hexahydro-2-methoxyazocine is added with stirring to a suspension of 3.5 g of N-phenyl-2,6-dimethyl-4-morpholine-carboximide-amide-hydroiodide in 10 ml of acetonitrile. The mixture is heated and vigorously stirred for 12 hours on a water bath. The acetone is evaporated off under reduced pressure, and the residue is recrystallised from a mixture of ethyl acetate and acetone to yield N-hexahydro-2(1H)-azocinylidene-N'-phenyl-2,6-dimethyl-4-morpholine-carboximide-amide-hydroiodide, which melts at 235° after recrystallisation from a mixture of isopropanol/ethyl acetate.

The starting material for this synthesis is produced as follows: 9 g of 2,6-dimethyl-morpholine is added to a suspension of 15 g of N-phenyl-S-methyl-isothioureahydroiodide in 50 ml of acetonitrile. The mixture is refluxed for 15 hours. The acetonitrile is evaporated off under reduced pressure, and the residue is recrystallised from a mixture of methylene chloride/ethyl acetate to yield N-phenyl-2,6-dimethyl-4-morpholine-carboximide-amidehydroiodide, which melts at 208°–210°.

EXAMPLE 6

3 g of morpholine is added with stirring to a suspension of 8.2 g of N'-(1-methyl-hexahydro-2(1H)-azocinylidene)-N-phenyl-S-methyl-isothiourea-hydroiodide in 30 ml of acetonitrile. The mixture is refluxed for 36 hours in an oil bath. The acetonitrile is evaporated off under reduced pressure, and the residue is recrystallised from a mixture of ethyl acetate and acetone to yield N'-(1-methyl-hexahydro-2(1H)-azocinylidene)-N-phenyl-4-morpholine-carboximide-amide-hydroiodide, which melts at 198° after recrystallisation from a mixture of isopropanol and ethyl acetate.

The starting material for this synthesis is produced as follows: 40 g of triethyloxoniumfluoroborate in 50 ml of methylene chloride is added, with cooling, to a solution of 14 g of 1-methyl-3,4,5,6,7,8-hexahydroazocin-2-one in 50 ml of methylene chloride. The reaction mixture is stirred for 18 hours in a nitrogen atmosphere, and ammonia is then introduced into the mixture for 3 hours. The reaction mixture is left to stand for 30 hours at room temperature, and the solvent is subsequently evaporated off under reduced pressure on a water bath at 40°. The crude 1-methyl-2-imino-3,4,5,6,7,8-hexahydroazocine is dissolved in 50 ml of acetonitrile, and 12 g of phenyl-isothiocyanate in 30 ml of acetonitrile is added with stirring at room temperature. The white crystalline material, which precipitates within almost 2 hours, is recrystallised from a mixture of ethyl acetate/isopropanol to yield N-phenyl-N'-(1-methyl-hexahydro-2(1H)-azocinylidene)-thiourea, which melts at 123°–125°.

10 g of methyl iodide in 30 ml of dioxane is added dropwise, with stirring, to a solution of 14 g of N-phenyl-N'-(1-methyl-hexahydro-2(1H)-azocinylidene)-thiourea in 50 ml of dioxane. The mixture is heated for 3 hours on a water bath. The dioxane is evaporated off under reduced pressure, and the residue is recrystallised from a mixture of ethyl acetate/acetone to yield N'-(1-methyl-hexahydro-2(1H)-azocinylidene)-N-phenyl-S-methyl-isothiourea-hydroiodide, which melts at 135°.

EXAMPLE 7

2.5 g of 3,4,5,6,7,8-hexahydro-2-methoxyazocine is added, with stirring, to a suspension of 3.5 g of N-(p-fluorophenyl)-4-morpholine-carboximide-amide-hydroiodide in 10 ml of acetonitrile, and the mixture is heated with vigorous stirring on a water bath for 12 hours. The acetonitrile is evaporated off under reduced pressure, and the residue is recrystallised from a mixture of isopropanol/acetone to obtain N-hexahydro-2(1H)-azocinylidene-N'-(p-fluorophenyl)-4morpholinecarboximide-amide-hydroiodide, which melts at 245°.

The starting material used for this synthesis is produced as follows: 3 g of morpholine is added to a suspension of 7.5 g of N-(p-fluorophenyl)-S-methyl-isothiourea-hydrochloride in 30 ml of acetonitrile. The mixture is refluxed with stirring for 15 hours. The acetonitrile is evaporated off under reduced pressure, and the residue is recrystallised from a mixture of acetone and ethyl acetate to yield N-(p-fluorophenyl)-4morpholinecarboximide-amide-hydroiodide, which melts at 210°.

EXAMPLE 8

1.5 g of 3,4,5,6,7,8-hexahydro-2-methoxyazocine is added, with stirring, to a suspension of 2.5 g of N-(m-trifluoromethylphenyl)-4-morpholine-carboximide-amidehydroiodide in 15 ml of acetonitrile. The mixture is stirred on a water bath and refluxed for 12 hours. The acetonitrile is evaporated off under reduced pressure, and the residue is recrystallised from a mixture of diethyl ether and ethyl acetate to yield N-hexahydro-2(1H)-azocinylidene-N'-(m-trifluoromethylphenyl)-4-morpholinecarboximide-amide-hydroiodide, which is converted into the free base and this into p-toluene sulfonate. The product melts at 202° after recrystallisation from acetone.

The starting material for this synthesis is produced as follows: 8 g of methyl iodide in 20 ml of dioxane is added to a solution of 11 g of N-(m-trifluoromethylphenyl)thiourea in 30 ml of dioxane. The reaction mixture is heated for 3 hours on a water bath. The dioxide is evaporated off under reduced pressure, and the residue is recrystallised from a mixture of isopropanol and ethyl acetate to yield N-(m-trifluoromethylphenyl)-S-methylisothiourea-hydroiodide, which melts at 220°.

3 g of morpholine is added to a suspension of 9 g of N-(m-trifluoromethyl-phenyl)-S-methyl-isothioureahydroiodide in 30 ml of acetonitrile. The mixture is refluxed for 15 hours with stirring. The acetonitrile is evaporated off under reduced pressure, and the residue is recrystallised from a mixture of acetone and ethyl acetate to yield (m-trifluoromethyl-phenyl)-4-morpholine-carboximide-amide-hydroiodide, which melts at 220°.

EXAMPLE 9

2 g of 3,4,5,6,7,8-hexahydro-2-methoxyazocine is added, with stirring, to a suspension of 3.5 g of N-p-tolyl-4-morpholine-carboximide-amide-hydroiodide in 15 ml of acetonitrile. The mixture is heated for 12 hours with vigorous stirring on a water bath. The acetonitrile is evaporated off under reduced pressure, and the residue is recrystallised from a mixture of acetone and ethyl acetate to yield N-hexahydro-2(1H)-azocinylidene-N'-p-tolyl-4-morpholine-carboximide-amide-hydroiodide.

The starting material for the above synthesis is produced as follows: 3.5 g of morpholine is added to a suspension of 9 g of N-p-tolyl-S-methyl-isothioureahydroiodide in 30 ml of acetonitrile. The mixture is refluxed for 15 hours with stirring. The acetonitrile is evaporated off under reduced pressure, and the residue is recrystallised from a mixture of isopropanol and ethyl acetate to yield N-p-tolyl-4-morpholine-carboximide-amide-hydroiodide, which melts at 218°–220°.

EXAMPLE 10

2.8 g of 1-aza-2-methoxy-1-cyclooctene is added to a suspension of 3 g of N-phenyl-1-(4-carbethoxypiperazine)-carboximide-amide-hydrochloride in 200 ml of acetonitrile, and the mixture is refluxed for 12 hours. The solvent is evaporated off under reduced pressure, and the residue is triturated with ethyl acetate to obtain, as colourless solid material, N-hexahydro-2(1H)-azocinylidene-N'-phenyl-1-(4-carbethoxypiperazine)-carboximide-amide-hydrochloride, which melts at 248°–249° after recrystallisation.

The starting material for the above synthesis is produced as follows: 9.6 g of N-carbethoxypiperazine in 15 ml is isopropanol is added to a solution of 8.7 g of S-methyl-phenylisothiourea-hydroiodide in 30 ml of isopropanol, and the solution is refluxed for 18 hours. The solvent is evaporated off under reduced pressure, and the residue is washed with petroleum ether. There is thus obtained N-phenyl-1-(4-carbethoxy-piperazine)-carboximide-amide-hydroiodide, which melts at 218°–219° after recrystallisation from a mixture of isopropanol/ethyl acetate.

The above product is treated with saturated aqueous potassium carbonate solution, and the mixture is extracted with methylene chloride. The extract is dried over anhydrous sodium sulfate; it is then filtered and the solvent is evaporated off under reduced pressure. The residue obtained is treated with hydrogen chloride in isopropanol to yield N-phenyl-1-(4-carbethoxypiperazine)-carboximide-amide hydrochloride, which melts at 251°–252° after recrystallisation from a mixture of methanol and ethyl acetate.

EXAMPLE 11

A mixture of 2.2 g of N-(p-methoxyphenyl)-1-(4-carbethoxy-piperazine)-carboximide-amide-hydroiodide and 1.4 g of 3,4,5,6,7,8-hexahydro-2-methoxyazorine is dissolved in 7 ml of acetonitrile, and the solution is refluxed for 10 hours. The clear solution is cooled and the resulting precipitate is filtered off. There is thus obtained N-hexahydro-2(1H)-azocinylidene-N'-(p-methoxyphenyl)-1-(4-carbethoxy-piperazine)-carboximide-amide-hydroiodide, which melts at 241°–242° after recrystallisation from a mixture of acetonitrile and ethyl acetate.

The starting material for the above product is obtained as follows: A mixture of 10 g of p-anisidine hydrochloride and 12.25 g of potassium thiocyanate in 100 ml of ethanol is heated for 16 hours. The reaction mixture is cooled and filtered. The residue is washed with water and recrystallised from methanol to yield a solid material melting at 226° and consisting of p-methoxyphenylthiourea. An amount of 5.3 g of the last-mentioned compound with 10 ml of methyl iodide in 20 ml of acetone is heated at 50° for 8 hours. The reaction mixture is cooled, and the precipitate is filtered off and then washed with acetone. The product obtained is S-methyl-N-(p-methoxyphenyl)-isothiourea-hydroiodide, which melts at 165°–166°.

A mixture of 6.4 g of S-methyl-N-(p-methoxyphenyl)-isothiourea-hydroiodide and 6.2 g of N-carbethoxypiperazine in 50 ml of acetonitrile is refluxed for 10 hours. The solvent is evaporated off under reduced pressure and the residue is triturated with ethyl acetate to yield N-(p-methoxyphenyl)-1-(4-carbethoxypiperazine)-carboximide-amide-hydroiodide, which melts at 156°–157° after recrystallisation from acetonitrile.

EXAMPLE 12

2.3 g of 3,4,5,6,7,8-hexahydro-2-methoxyazocine is added with stirring, to a solution of 2.4 g of N-phenyl-1-(4-methyl-piperazine)-carboximide-amide-hydroiodide in 6 ml of acetonitrile, and the mixture is refluxed for 12 hours. The reaction mixture is cooled, and diluted with 10 ml of ethyl acetate. There is formed an amorphous solid material which, after trituration with acetone, becomes crystalline. The product obtained is N-hexahydro-2(1H)-azocinylidene-N'-phenyl-1-(4-methyl-piperazine)-carboximide-amide-hydroiodide, which melts at 222°–223° after recrystallisation from acetonitrile.

The starting material used for the synthesis of the above product is produced as follows: A mixture of 10 g of S-methyl-phenylisothiourea-hydroiodide and 7.6 g of N-methylpiperazine is dissolved in 50 ml of isopropanol, and the solution is refluxed for 10 hours. The solvent is evaporated off under reduced pressure, and the residue is treated with petroleum ether to yield 1-(4-methyl-piperazine)-N-phenyl-carboximide-amide-hydroiodide, which melts at 231°–232° after recrystallisation from a mixture of acetonitrile and ethyl acetate.

What is claimed is:

1. A guanidine derivative of the formula

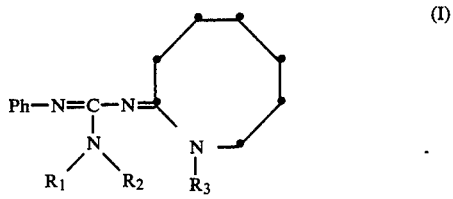

wherein Ph is phenyl, the group —NR$_1$R$_2$ is morpholino, and R$_3$ is hydrogen, or methyl, or a tautomeric compound or therapeutically useful salt thereof.

2. A compound as claimed in claim 1 being N-hexahydro-2(1H)-azocinylidene-N'-phenyl-4morpholinecarboximide-amide as well as a therapeutically useful salt thereof.

3. A therapeutic composition for the treatment of hyperglycaemia comprising an effective amount of an hypoglycaemic active compound of formula I as claimed in claim 1 togehter with a pharmaceutically acceptable excipient.

4. A therapeutic composition as defined in claim 3, wherein the hypoglycaemic active compound is N-hexahydro-2(1H)-azocinylidene-N'-phenyl-4-morpholinecarboximide-amide.

5. A method for the treatment of hyperglycaemia, which comprises administring to a living body suffering from hyperglycaemia an effective amount of a compound of formula I as claimed in claim 1.

* * * * *

UNITED STATES PATENT AND TRADEMARK OFFICE
CERTIFICATE OF CORRECTION

PATENT NO. : 4,626,537

DATED : DECEMBER 2, 1986

INVENTOR(S) : KRISHNA G. DAVE AND THOMAS GEORGE

It is certified that error appears in the above—identified patent and that said Letters Patent is hereby corrected as shown below:

On the cover page, Item [63] line 1 should read -- Continuation of Ser. No. 660,769, Oct. 15, 1984, abandoned --.

Signed and Sealed this

Thirteenth Day of October, 1987

Attest:

DONALD J. QUIGG

*Attesting Officer*    *Commissioner of Patents and Trademarks*